United States Patent [19]
Kronick et al.

[11] 3,939,350
[45] Feb. 17, 1976

[54] FLUORESCENT IMMUNOASSAY EMPLOYING TOTAL REFLECTION FOR ACTIVATION

[75] Inventors: Melvyn N. Kronick; William A. Little, both of Palo Alto, Calif.

[73] Assignee: Board of Trustees of the Leland Stanford Junior University, Stanford, Calif.

[22] Filed: Apr. 29, 1974

[21] Appl. No.: 465,009

[52] U.S. Cl. ............... 250/365; 250/302; 250/304; 356/36
[51] Int. Cl.² ........................................... G01T 1/20
[58] Field of Search ........... 250/302, 304, 365, 461; 23/230 R, 230 B; 356/36

[56] References Cited
UNITED STATES PATENTS

| | | | |
|---|---|---|---|
| 3,684,377 | 8/1972 | Adams et al. | 356/36 |
| 3,719,410 | 3/1973 | Kallet | 356/36 |
| 3,814,939 | 6/1974 | Parker et al. | 250/304 |

*Primary Examiner*—Archie R. Borchelt
*Attorney, Agent, or Firm*—Townsend and Townsend

[57] ABSTRACT

Receptors are employed to which one or more fluroescent molecules are bound. When the receptors are bound to the epitopic sites on the surface and light of predetermined wave length is directed toward the surface, the fluorescing molecules are activated and fluoresce.

In carrying out an assay, receptor is combined with an unknown suspected of containing molecules having the same epitopic sites bound to the surface. The receptor will bind to these molecules reducing the number of receptor sites available for binding to the epitopic sites on the surface. When the assay medium is contacted with the surface, the amount of receptor which binds to the surface, will be a function of available binding sites and, therefore, to the number of the molecules present in the unknown. Upon irradiation of the surface, substantially only the fluoroescent molecules bound to the surface will fluoresce. By monitoring the fluorescence, one can determine the presence and number of molecules of interest present in the unknown.

The apparatus consists of a transparent solid sheet, conveniently as part of or optically connected to a prism, a light source set at an angle to provide total internal reflection at the sheet, a cell which includes the reflecting surface as a wall, and a fluorescence detector. Various optics and filters may be employed to modify the light source beam and the fluorescence beam.

This work was carried out under a grant of the National Science Foundation.

15 Claims, 4 Drawing Figures

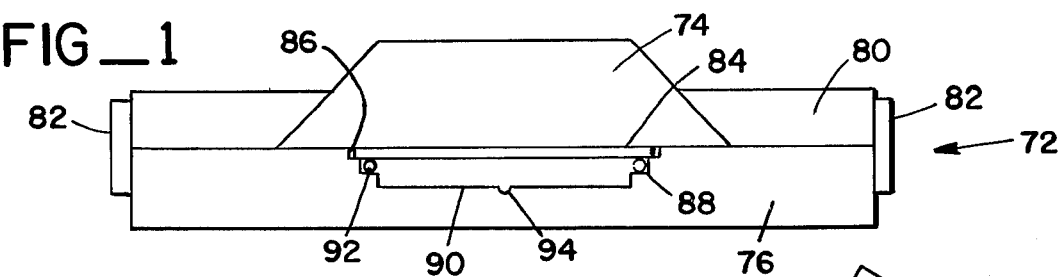
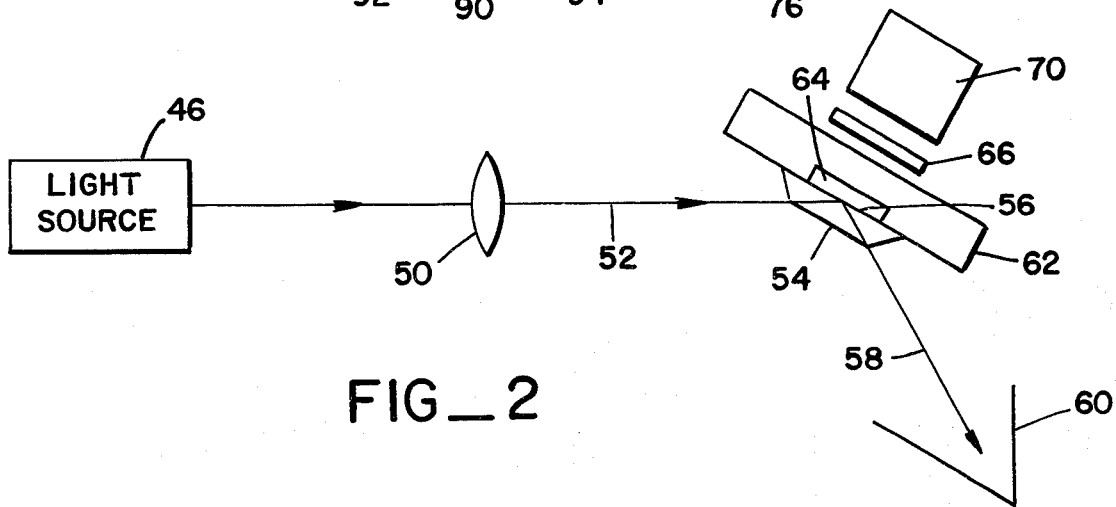
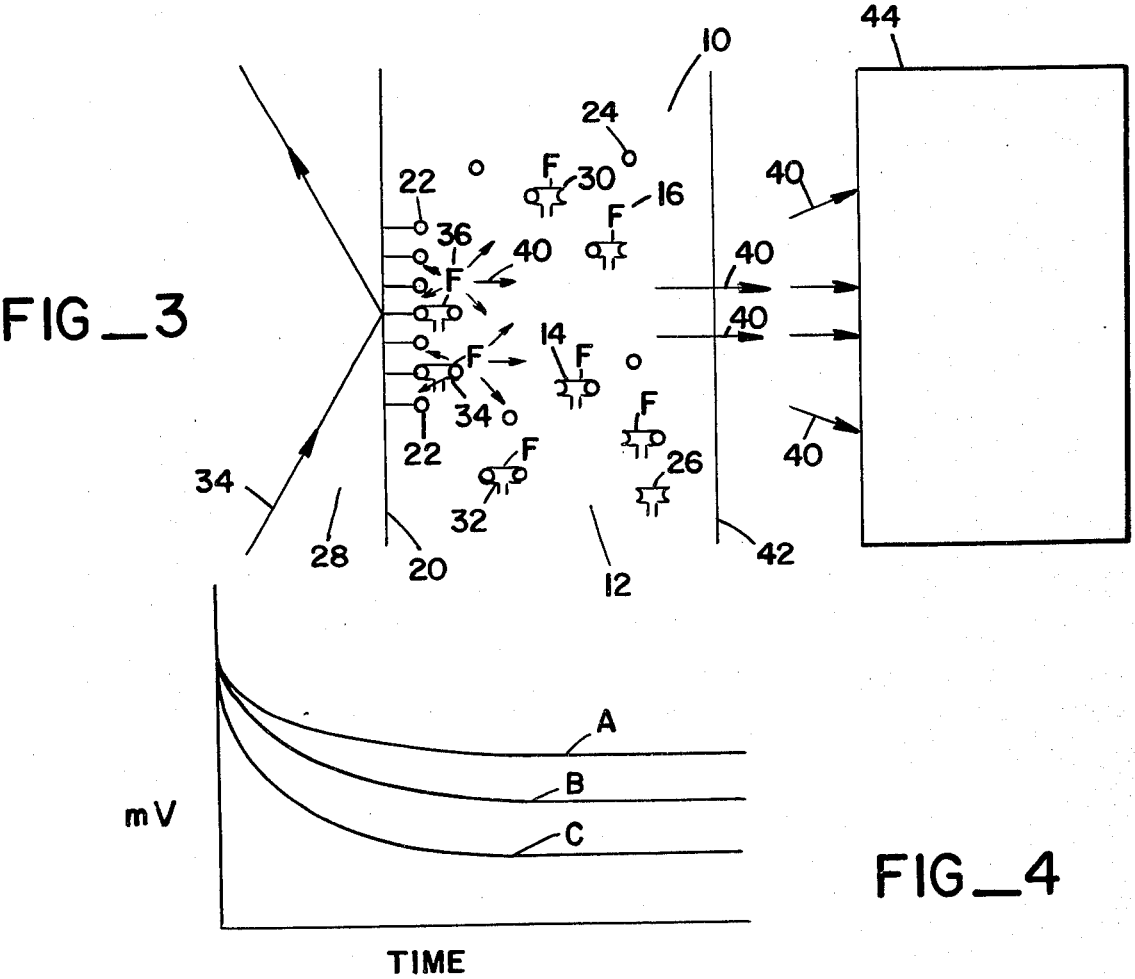

FLUORESCENT IMMUNOASSAY EMPLOYING TOTAL REFLECTION FOR ACTIVATION

BACKGROUND OF THE INVENTION

1. Field of the Invention

There is a continuing and expanding interest in the ability to measure small quantities of naturally occurring and synthetic compounds or compositions. A broad category of methods fall in the classification of immunoassays. These methods depend on the ability of a receptor, usually an antibody, to recognize a particular spatial and polar configuration and bind to such configuration. As a result of this binding, the resulting complex can be differentiated from molecules which are present, which are not bound to the receptor.

For purposes of convenience, the compound to be determined will be referred to a "ligand." In immunoassays, a ligand analog is provided which is capable of competing with the ligand for the receptor. That is, the ligand analog has a spatial and polar configuration analogous to the ligand and is also tagged, so as to allow for its detection. In the immunoassay, any ligand present in an unknown and ligand analog compete for the receptor. The amount of ligand analog bound to receptor will be related to the amount of ligand present in the unknown. Ligand analog bound to receptor can be distinguished from ligand analog which is unbound.

In one technique, referred to as radioimmunoassay, the ligand analog has a radioactive atom. Where the receptor is antibody, which is the conventional receptor, ligand analog bound to antibody can be separated from ligand analog which is unbound. By determining the distribution of radioactive labeled ligand, between bound and unbound, one can determine the amount of ligand present in the unknown.

An alternative method employs a stable free radical tag, such as a small nitroxide molecule. With small ligands, molecular weights below about 50,000, the rate of tumbling of the ligand analog in solution is sufficiently fast, so as to provide a relatively sharp peak in the EPR spectrum of the free radical. When the ligand analog is bound to receptor, which is normally of high molecular weight, the peak is broadened to a much greater half-width. Therefore, by measuring a point near the maximum of the peak, the height at that point can be related to the distribution of bound and unbound ligand analog. This in turn can be related to the concentration of ligand in an unknown.

A third technique employs an enzyme as the detector. The technique can be carried out homogeneously or heterogeneously. In U.S. Pat. Nos. 3,654,090 and 3,791,932, heterogeneous systems are described. The heterogeneous system requires binding one of the reagents involved in the determination to a solid support, for example, the receptor. By allowing competition for the receptor bound to solid support between the ligand and the ligand analog, and separating the solid support, one can then determine the enzyme activity in the supernatant. The amount of ligand analog remaining in the supernatant, as determined by the enzyme activity in the solution, is related to the amount of ligand present.

An alternative system is homogeneous. This is based on a reduction in enzyme activity, when ligand analog is bound to receptor. The reduction in enzyme activity is related to the amount of ligand analog bound to receptor. By using standards, which is conventional with the other immunoassay techniques, one can relate change in enzyme activity to the amount of ligand present in the unknown.

Each of the above systems have advantages and disadvantages as applied to specific situations. In one or more of the systems, expensive equipment is required. Working with radioactive materials is undesirable. Furthermore, the radioactive materials have only a limited shelf life. The free radical technique is limited as to the molecular weight of the ligand. The enzyme technique is subject to interfering substances present in the unknown. There is, therefore, a continued interest in finding new systems which may avoid the deficiencies of the earlier systems, and have substantial advantages in particular applications.

2. Description of the Prior Art

Radioimmunoassays are described in Murphy, J. Clin. Endocr., 27, 973 (1967); ibid, 28, 343 (1968). Free radical immunoassays are described in U.S. Pat. No. 3,690,834. Enzyme immunoassays are described in U.S. Pat. Nos. 3,654,090 and 3,791,932 and U.S. Pat. Application Ser. No. 143,609, filed May 14, 1971, now abandoned. Techniques employing total internal reflection are described in Herrick, et al., Anal. Chem., 45, 687 (1973) and Amer. Laboratories, 5, 63 (1973). See also, Kronick, et al., Bull. of the Amer. Physical Society, 18, 782 (1973).

SUMMARY OF THE INVENTION

Method and apparatus are provided for carrying out immunoassays, using the amount of fluorescence as an indication of the presence of a compound or composition ("ligand") to be detected. A ligand, having one or more epitopic sites, is bound to the flat surface of an optically transparent sheet. The surface is contacted with an aqueous solution—assay medium—containing the unknown and antibody to the ligand. The antibody is tagged with fluorescing molecules. Depending on the amount of ligand present in the solution, the available sites for binding to the surface will vary, and the amount of antibody bound to ligand on the surface will proportionately vary, when the surface is contacted with the assay medium.

The sheet is irradiated with light at the wave length of absorption of the fluorescing molecule bonded to the antibody. The angle of irradiation provides total internal reflection, so that fluorescence can occur within only a few hundred Angstroms of the surface. By measuring the amount of fluorescence, for example, with a photomultiplier tube, the amount of ligand present in the solution can be determined.

The apparatus is comprised of a light source, an optically transparent sheet in appropriate juxtaposition to provide total internal reflection, a cell having the transparent sheet as one wall, and a light detector situated so as to receive fluorescent light from the cell.

BRIEF DESCRIPTION OF THE DRAWINGS

FIG. 1 is an elevational cross-sectional view of a cell and prism;

FIG. 2 is a diagrammatic view of an immunoassay apparatus;

FIG. 3 is a stylized illustrative view of the reaction occurring in the cell;

FIG. 4 is a plot of three curves obtained following the method of this invention.

DESCRIPTION OF THE SPECIFIC EMBODIMENTS

A method and apparatus are provided for carrying out immunoassays, whereby the amount of fluorescence obtained from a sample cell is related to the amount of material being determined. In discussing the method, the following terminology will be employed. A compound or composition recognizable by a single receptor, haptens or antigens, will be referred to as ligand. "Receptors" are high molecular weight molecules, usually proteins, which are capable of binding to a particular spatial and polar organization. For the most part, receptors are antibodies and antibodies will be illustrative of receptors.

The immunoassay is carried out by providing a competition for receptor to which fluorescer molecules are bound, between epitopic or determinant sites of molecules in an aqueous buffered assay medium and the same epitopic sites bound directly or indirectly to a transparent surface. The transparent surface serves as one wall of a cell containing the assay medium. The assay medium is constituted of an aqueous solvent, normally buffered, fluorescer-bound-receptor, unknown to be assayed, and other additives which may be appropriate in particular situations.

By appropriate choice of the material for the transparent surface, a material having a refractive index greater than the assay medium, the surface can be irradiated with light at an angle which provides total internal reflection. Under conditions of total internal reflection, only fluorescent molecules within a few hundred Angstroms of the surface will be activated and fluoresce. The number of receptor molecules bound to the surface, and, therefore, the number of fluorescent molecules sufficiently close to the surface to be activated will be proportional to the number of molecules to which receptor is bound in the assay medium.

By measuring the amount of fluorescence upon irradiation, one can obtain a determination of the presence of molecules in the unknown having the same epitopic sites as the molecules bound to the surface. By using standards having known amounts of such molecules, one can prepare a curve relating the amount of fluorescence to the amount of such molecules present in the assay medium.

The method employed in the immunoassay depends upon total internal reflection. At an interface between two materials of different refractive indicies, the angle of incidence is related to the angle of reflection by the following formula:

$n_1 \sin\theta_1 = n_2 \sin\theta_2$ where $n_1$ and $n_2$ are the refractive indicies of the two materials and $\theta_1$ and $\theta_2$ are the angles from the norm which the incident radiation makes at the interface. When the sine of the angle of incidence is equal to or greater than the ratio of the refractive indicies, $n_2/n_1$, total internal reflection occurs, and the light does not penetrate the second medium.

Some light energy does in fact penetrate the second medium over relatively short distances, usually not exceeding about 1,000A. Depending upon the variables involved, the distance of penetration of light energy can be diminished to as little as 500A. If a fluorescing molecule is positioned at the interface in the second medium, so as to be within the range of light energy which penetrates the second medium, when the wave length of the light is within the adsorption peak of the fluorescing molecule, the fluorescing molecule will fluoresce. Fluorescing molecules that are outside this narrow band will not fluoresce.

The subject immunoassay can be used for detecting a wide variety of compounds, both haptenic and antigenic. The significant factor is that a receptor can be provided which recognizes a specific spatial and polar organization—an eptiopic or determinant site—and is capable of having one or more fluorescing molecules bound to it.

In the subject invention, for the most part, the receptors will be macromolecules, which have sites which recognize specific structures. The recognition of the specific structures will be based on Van der Waals forces, where the receptor provides a specific spatial environment which maximizes the Van der Waals forces; dipolar interactions, either by permanent or induced dipoles; hydrogen and ionic bonding; coordinate covalent bonding; and hydrophobic bonding.

The macromolecules of greatest interest are proteins and nucleic acids which are found in cell membranes, blood, and other biological fluids. These compounds include enzymes, antibodies, ribonucleic acid (RNA), deoxyribonucleic acid (DNA), and natural receptors. Of particular interest are the antibodies, particularly the $\gamma$-globulins, which have two binding sites or can be split in two so as to have a single binding site.

The receptors are modified with fluorescing molecules. Methods for linking fluorescing molecules to proteins are well-known in the art. Various linking groups include activated carboxylic acid groups, for example, by employing the mixed anhydride or with carbodiimide, isothiocyanate, nitrophenyl or nitrobenzyl esters, or the like. Many of the commercially available fluorescing compounds have groups for linking to proteins. The preparations are normally carried out under mild conditions in aqueous media.

In choosing the fluorescing compound to be linked to the antibody, a number of considerations come into play. If the ligand to be determined fluoresces, then the choice of fluorescer will be such as to have a longer wave length higher absorption maximum than the ligand. Also, the fluorescer should not enhance nonspecific binding to glass surfaces or other proteins. In addition, since proteins adsorb at a wave length of about 280nm, the fluorescer should have an adsorption maximum above 300nm, usually above 350nm and preferably above 400nm. The extinction coefficient should be greatly in excess of 10, preferably in excess of $10^3$, and particularly preferred, in excess of $10^4$. The number of fluorescing molecules per receptor will be from about 1 to 40, usually from about 1 to 30, and preferably about 5 to 25.

A number of different fluorescers are described in Brand, et al., Annual Review of Biochemistry, 41, 843–868 (1972) and Stryer, Science, 162, 526 (1968).

One group of fluorescers of particular interest are xanthene dyes, which include the fluoresceins, derived from 3,6-dihydroxy-9-phenylxanthydrol and rosamines and rhodamines, derived from 3,6-diamino-9-phenylxanthydrol. The rhodamines and fluoresceins have a 9-o-carboxyphenyl group and are derivatives of 9-o-carboxyphenylxanthydrol.

These compounds are commercially available with substituents on the phenyl group which can be used as the site for bonding or as the bonding functionality. For example, amino and isothiocyanate substituted fluorescein compounds are available.

Another group of fluorescent compounds are the naphthylamines, having an amino group in the alpha or beta position, usually alpha position. Included among the naphthylamino compounds are 1-dimethylaminonaphthyl-5-sulfonate, 1-anilino-8-naphthalene sulfonate and 2-p-toluidinyl-6-naphthalene sulfonate.

Methods for conjugating fluorescing molecules for protein may be found in Rinderknecht, Nature, 193, 167 (1962); Goldman, Fluorescent Antibody Techniques, Academic Press, New York (1968); and Smith, et al., J. Bacteriol., 83, 1358 (1962).

The compounds of interest to be analyzed can be widely varied including naturally occurring and synthetic drugs, including drugs of abuse, e.g. hypnotics and alkaloids, hormones, metabolites, particularly of diseased states, pesticides, vitamins, and the like. Groups of compounds of interest include alkaloids, particularly opiates and cocaine, steroids, epinephrine and derivatives, proteins, e.g. insulin, human chorionic gonadotrophin, CEA, angiotensin and the like, synthetic drugs of abuse, e.g. methadone, amphetamine, and barbiturates, amino acids, e.g. tri-or tetraiodothyronine, therapeutic drugs, e.g. antibiotics, diphenylhydantoin glutethimide, primadone, and the like.

A particular group of compounds of interest are haptens of from about 125 to 1,000 molecular weight, usually not more than 750 molecular weight, having from 1 to 10, usually 1 to 8 heteroatoms, which are primarily oxygen, sulfur, nitrogen, phosphorus, alkali metal cations, e.g. sodium and potassium, and halide, e.g. chloride, bromide and iodide. Of particular interest are those compounds having oxygen, sulfur, nitrogen, and halide.

Another group of compounds are the poly(amino acids)—polypeptides and proteins—usually of from about 1,000 to $10^6$ molecular weight, which includes antigens, hormones, enzymes and the like.

The ligand can be either bonded directly or indirectly to the transparent surface. Where the transparent surface is a glass, e.g. quartz, the surface can be activated with a wide variety of silyl compounds. Preferably, silyl esters are employed having one group having a silyl-carbon bond. To this group is bonded a functionality, such as carboxy, amino, or the like, which may be used directly or modified for linking to the ligand. For methods of activating a glass surface, see Weetal, Nature, 223, 959 (1969). Illustrative activating groups include 3-cyanopropyl triethoxysilane, 3-aminopropyl trimethoxysilane, 4-ethoxycarbonylbutyl triethoxysilane, and the like.

Where the surface is an organic polymer, the manner of activation will depend upon the particular nature of the polymer. For example, hydrocarbons can be lightly halogenated and the halogen displaced with amino groups, thio groups, or the like, to introduce the functionality which can then be bonded to the ligand.

In many instances, it will be satisfactory to contact the surface with an aqueous solution of the antigenic protein or hapten conjugated protein and allow the protein to nonspecifically adsorb onto the surface. Where the bonding is strong enough, the assay can be carried out, without significant desorption of the protein occurring during the period of measurement.

Irrespective of whether the ligand is a protein, it is desirable to have a thin protein coat on the transparent surface which serves as the interface between the surface and the assay medium. Where the ligand is a protein, the ligand itself may serve as the protein coating. Where the ligand is other than a protein, the ligand may be bonded to a protein, for example, albumin, and the albumin in turn bonded to the transparent surface. The amount of ligand bonded to the protein will be at least one ligand per 50,000 molecular weight, usually at least about one ligand per 20,000 molecular weight, and more usually at least one ligand per 15,000 molecular weight.

The slides which are employed in the invention will appear as follows:

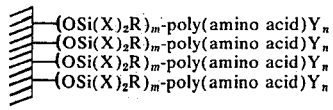

The line designates a surface of an optically transparent slide, e.g. glass, quartz, or polyolefin, generally of from about 0.5mm to 2mm thickness and being regularly shaped having its smallest dimension of about 2mm and its largest dimension of about 30mm, generally having dimensions ranging from about 5 to 25mm. Either the poly(amino acid) is noncovalently bonded to the surface ($m=0$) or bonded to the surface are a plurality of polysiloxane groups which are in turn bonded to the poly(amino acid) ($m=0$).

X intends an alkoxy group of from one to three carbon atoms.

R is a linking group, conveniently hydrocarbon, of from 2 to 10 carbon atoms, usually 2 to 6 carbon atoms, bonded to the poly(amino acid) by a peptide, urea or thiourea linkage;

poly(amino acid) intends a polypeptide or protein of from about 20,000 to 300,000, usually 50,000 to 200,000 molecular weight, which will generally be an albumin or globulin;

Y is a hapten of from about 125 to 1,000 molecular weight bonded to the poly(amino acid) through a peptide, urea or thiourea group, having from about 1 to 10, usually 1 to 8 heteroatoms which are oxygen, sulfur, nitrogen, phosphorous, alkali metal cation, e.g. sodium and potassium, and halide, i.e., chlorine, bromine and iodine, usually oxygen, sulfur, nitrogen and halide; and $n$ is 0 when the poly(amino acid) is the ligand, or when Y is the ligand, on the average from one to the molecular weight of the poly(amino acid) divided 1,000, more usually divided by 2,000, and preferably at least two.

The slide surface will be substantially completely covered with protein to avoid nonspecific binding. The protein may be linked by a single bond to the surface depending on the size of the protein, the number of silyl groups per unit area and the like.

Various transparent optical elements may be employed as the light receiving element, for example, a prism. While the surface of the prism, which serves as the interface or cell wall may be modified for protein bonding, it is more convenient to use a small disc or slide which may be optically coupled to the prism through a liquid of the same refractive index and mechanically held in position abutting the prism surface. The slide then serves as the interface between the assay medium and the surface at which total internal reflection occurs. The slide surface is activated for chemical bonding as previously described, and the ligand or ligand modified protein bound to the surface.

By appropriate masking of the surface, or use of a grid providing a plurality of chambers, one can produce a slide to which different ligands have been bonded at different sites. In this manner, a single slide can be used to detect a number of different ligands in the assay medium simultaneously. Furthermore, by using an appropriately thin prism, the number of reflections can be multiplied, so that the light rays are reflected from the surface a plurality of times. Thus, at each reflection site, there will be light energy to activate any fluorescent molecules which are present. By appropriate use of slits to limit the light received by the fluorescent light receiver, one could scan the various areas to determine whether fluorescence is occurring at a specific area. Also, the sensitivity of the assay is enhanced by multiple reflection.

Prior to carrying out an assay, the apparatus is assembled. A slide having the appropriate ligand bonded to one side is coated on the other side with a fluid having the same refractive index as the slide and prism. The slide is then pressed against the bottom of the prism to avoid any air bubbles. The prism is mounted on the holder, which will be described subsequently, and the cell filled with the assay medium. The light source is then turned on in order to irradiate the slide surface and the current from the photomultiplier tube recorded until a substantially constant value is obtained. The value indicates the amount of fluorescence from the surface.

For the assay medium, an aqueous buffered solution is provided, normally being buffered in the range of about pH 6–9, particularly pH 7–8, where the binding of the receptor is maximized. If the assay medium is not naturally buffered, various buffers may be employed, such as borate, tris, phosphate, carbonate, and the like. Buffer concentrations generally range from about 0.01 to 0.5, usually not exceeding about 0.2M.

The appropriate antibody or antibodies, tagged with fluorescent molecules are introduced into the medium. Binding site concentrations (as determined for example by radioimmunoassay) will generally range from about $10^{-2}$ to $10^{-14}$, more usually from about $10^{-4}$ to $10^{-12}$M. The particular binding site concentration will depend upon the binding constant of the antibodies, the concentration of interest of ligand, the sensitivity desired for the assay, and the like. The ligand concentration to be determined will generally vary from $10^{-2}$ to $10^{-14}$M depending upon the ligand to be determined.

In the assay medium, the ratio of receptor to ligand will vary widely, usually being at least about one receptor site per 1,000 ligand molecules, more usually one receptor site per 500 ligand molecules, frequently not more than about one receptor site per 50 ligand molecules, and not more than about 1,000 receptor sites per epitopic site of the ligand.

While various orders of addition may be employed, the preferred protocol is to combine the unknown with receptor in an aqueous buffered medium to allow sufficient time for the ligand to bind to the receptor. Depending upon the concentrations involved, the time may vary from about 0.5 min to 1 hour or more. The solution may then be introduced into the cell chamber preferably thermostated at a temperature in the range of about 20°–40°C, and the amount of fluorescence recorded until a relatively stable value is obtained. As previously indicated, by use of known amounts of the ligand, a standard curve can be obtained to which values of fluorescence can be related to concentration of ligand present in the unknown.

For further understanding of the invention, the drawings will now be considered. The events of the assay are depicted in FIG. 3. In FIG. 3, a portion of a cell 10 is shown. The cell contains an aqueous buffered solution 12 which contains antibodies 14 to which have been bonded fluorescing groups 16 depicted as F. The cell has a transparent wall 20 to which has been bound a plurality of ligands 22, depicted as circles. The transparent wall 20 is part of a prism 28 of which only a portion is shown. In the solution 12 are a plurality of free ligands 24.

The antibody 14 present in the solution has two sites for binding to the ligand 24. Some antibody 26 in the solution has both sites free, while other antibody 30 and 32 have one and two sites filled with ligand, respectively. The antibody with both sites free 26 and one site free 32 are capable of binding to the ligand 22 bound to the surface 20. Therefore, at equilibrium, there will be some antibody bound to the ligand 22, which is proportional to the amount of ligand 24 in solution. In effect, ligand 24 limits the concentration of available antibody for binding to ligand 22 bound to the surface Light ray 34 is of a wave length at or near the adsorption maximum of the fluorescing group 16. The light has a sufficiently small incident angle, so as to provide total internal reflection at the interface between the prism 22 and the aqueous solution 12. Light energy does penetrate a short distance past the transparent wall 20 so as to activate fluorescing groups 36 bound to the wall 20 through ligand 22. The activated fluorescing groups 36 emit light rays 40 which pass through transparent wall 42 of the cell 10 and are detected by a photomultiplier tube 44. The amount of radiation is translated into an electrical signal, which can be recorded.

By employing known concentrations of ligand and determining the amount of fluorescent radiation related to a known amount of ligand, a standard curve can be prepared which relates fluorescent radiation to concentration. One can then quantitate the amount of ligand in relation to the amount of fluorescence observed.

The type of curves one obtains is depicted in FIG. 4. Time is the abscissa and the ordinate is proportional to the amount of fluorescence. Initially one observes a null point. As the number of antibodies bound to the surface increases, the fluorescence increases with an increasing value along the ordinate until an equilibrium is approached, resulting in a substantially flat portion of the curve.

In FIG. 2, a device is depicted diagrammatically. A laser source 46 provides light of a wave length of the adsorption band of the fluorescer molecules. The beam is spread by an optical system 50, so as to provide coverage over a wider area. The beam 52 passes through prism 54 and is reflected from interface 56. The reflected light beam 58 is then transmitted to a light dump 60.

In those instances where the intensity of the light from the light source may fluctuate, a portion of the light beam can be deflected and its intensity monitored. By appropriate circuitry, the value obtained from the photomultiplier tube monitoring the fluroescence can be divided by the fraction obtained by dividing the momentary intensity by a base intensity. In this way, the value obtained for the amount of fluorescence is obtained independent of fluctuations of intensity in the light source.

Prism 54 is mounted on housing 62 which has chamber 64 sealed by face 56. The housing 62 is transparent or can be supplied with a window behind chamber 64 to allow for light transmission.

A light filter 66 is provided to cut out scattered light other than light within the fluorescing band of the fluorescer. A photomultiplier tube 70 or other light detector can be employed to measure the fluorescent light emanating from chamber 64. While the light detector is depicted as receiving light from the fluorescing molecules on the side of the slide opposite the prism, the light detector can be positioned on the same side as the prism or two or more light detectors may be employed to increase the fluorescent signal. It is possible to receive fluorescent light through the prism.

In FIG. 1 is depicted a cell housing 72 which has a prism 74 mounted on a base 76. The prism is secured in position by frame 80 which is locked to base 76 by fasteners 82. A small transparent disc 84 is optically coupled to prism 74 by means of a solution having the same refractive index as the transparent disc. Base 76 has a stepped cavity to provide a first recess 86 to accommodate the transparent disc 84 and a chamber 90. An O-ring 92 is included in the chamber 90, supported by step 88, and presses against the transparent disc 84 to provide a watertight seal. Channel 94 provides access to the chamber for filling or evacuating the chamber.

The prism which is employed can be of any optically transparent material, such as glass, quartz, polyolefin plastics, e.g. poly-4-methyl-1-pentene, etc., so long as it has the appropriate refractive index to permit a reasonable angle of incidence to provide total internal reflection. The disc which is employed should also be made of the same material. Various coupling liquids can be employed, which have the same refractive index as the prism and disc. The holder which restrains the prism and provides the cell chamber, can be of any convenient material, having the appropriate transparency, or can be machined to provide a window.

Experimental

The following examples are offered by way of illustration and not by way of limitation.

(All temperatures not otherwise indicated are in Centigrade. All parts and percentages not otherwise indicated are by weight.)

The apparatus employed in the following experiments used a helium-cadmium laser. Four lenses were used in tandem to spread the beam. In the order extending away from the laser, the lenses were cyl. Rolyn lenses nos. 14.0050, 14.0100, 10.0050, and 10.0385 respectively, with focal lengths 22.2mm, 40.0mm, 25.4mm and 200mm respectively. A quartz prism was set at an angle to provide total internal reflection. The quartz prism was 1 ⅝ inches long, 1 ½ inches wide, ½ inches high, and had an angle of 70°. The prism was mounted on a sheet of plexiglass one-quarter inch thick, which had a stepped wall chamber. The distance from the surface for the successive steps was 0.065, 0.120, 0.170, and 0.250in, with the first step having a cross-section 1 ⅝ inches by 1 ½ inches, the second step had a cross-section of 1 in by 1 in, with the next steps being circular and having radii of seven-sixteenths inch and three-eighths inch respectively. The quartz prism resides in the area provided for the first step, while the disc resides in the area provided for the second step. The third step contains an O-ring which seals the area about the disc so as to avoid leakage. The cell volume which contains the assay medium is approximately 1ml.

A Baird-Atomic B-5 barrier filter and a green gelatin filter are placed between the plexiglass holder, and the fluorescent light counter so as to filter out light of undesired wave lengths. Adjacent to the filter to receive the light is an EMI 9558B photomultiplier tube. The current is monitored by a 425A HP microvolt ammeter. The light reflected from the quartz prism surface is fed to a beam dump.

Quartz slides 1 by 1 by 1/16 inch in thickness are prepared as follows. The slides are cleaned with Alconox cleaning solution, followed by rinsing with tap water and then distilled water. The slides are then rinsed with ethanol and placed in a rack where they are washed with condensed isopropanol vapors. This treatment is maintained for about 5 min. The slide is then dipped into a one weight percent aqueous solution of 3-aminopropyl triethoxy silane at pH 3. After standing in the solution for about 10 min, the solution is siphoned off, and the slide is baked in vacuo at 60° for 6 hours or more.

p-Arsanilic acid conjugated to egg albumin by peptide bonds is employed as a source of hapten, there being about 20 p-arsanilic acid groups bonded per molecule of egg albumin. The slide is placed into a 2.5% glutaraldehyde solution at pH 7.0, .05M phosphate having about 1mg/ml egg albumin conjugate and allowed to stand overnight.

The slide is then removed from the solution, rinsed with water, the water allowed to drain off, and the top face of the slide wiped clean with absorbent paper. A drop of cyclohexanol is placed on the dry surface and the slide place against the prism surface.

A cell is filled with the appropriate assay solution, and the photomultiplier tube set at an appropriate voltage. Using different slides for each determination, the following conditions were employed. The photomultiplier tube was at 1,000 volts. A Hewlett Packard 425A microvolt ammeter was employed employing the 10 microamp scale. The normalized signal from the ammeter is displayed on an X-Y recorder.

The antibody employed in the above experiment had an average of about 1.9 fluorescing molecules per antibody. The antibody was obtained from Calbiochem employing Lot No. 539859. Fluorescein isothiocyanate was coupled in accordance with the procedure set forth in Rinderknecht, supra.

The following table indicates the results.

TABLE I

| Ab $M \times 10^{-5}$ | Rp[1] $M \times 10^{-6}$ | Reading mV |
|---|---|---|
| 1.2 | — | 18.5 |
| 0.6 | — | 10 |
| 0.3 | — | 7 |
| 1.1 | 9 | 8 |

[1]p-arsanilic acid

Considering FIG. 4, A and C would be the curves for low and high concentrations respectively for antibody without ligand present and B would be the curve for substantially the same concentration of antibody as employed in C with ligand present, all other things being constant.

The above results demonstrate that with varying concentrations of antibody in the solution, the amount of fluorescence varys proportionately. Furthermore, by reducing the amount of available antibody, by adding p-arsanilic acid to the solution, the presence of the ligand is detectable by a reduction in the amount of fluorescence.

In accordance with the subject invention, a sensitive assay is provided for detecting small amounts of ligand employing a fluorescer technique. The apparatus employed is simple and inexpensive. The method is easily carried out and enjoys the specificity enjoyed by other immunoassay techniques.

Although the foregoing invention has been described in some detail by way of illustration and example for purposes of clarity of understanding, it will be obvious that certain changes and modifications may be practiced within the scope of the appended claims.

What is claimed is:

1. A method for determining the presence of a ligand in an unknown suspected of containing said ligand, which comprises:
   combining in an aqueous assay medium, said unknown and receptor for said ligand, said receptor having at least on the average one fluorescing molecule bound to each receptor molecule;
   contacting said assay medium with one side of an optically transparent surface having a plurality of ligand analogs bound to said surface in contact with said assay medium, wherein the optically transparent surface has a refractive index greater than the refractive index of said assay medium;
   irradiating said surface with light having a wave length absorbed by said fluorescing molecule, on the side of said surface opposite said assay medium, and at an angle to said surface to provide total internal reflection; and
   measuring the amount of fluorescent light emitted from said surface, wherein the amount of fluorescent light is a function of the amount of ligand present in said assay medium.

2. A method according to claim 1, wherein said optically transparent surface is coated with protein on said one side.

3. A method according to claim 1, wherein said receptor is an antibody and said ligand is of a molecular weight in the range of 125 to 1,000.

4. A method according to claim 3, wherein said antibody has from 1 to 40 fluorescing molecules on the average per antibody molecule.

5. A method according to claim 1, wherein said assay medium is buffered in the range of 6 to 9, and said ligand is bound to protein which is bound to said surface.

6. A method according to claim 5, wherein said fluorescing molecule has an absorption maximum greater than 300nm.

7. A method according to claim 6, wherein said fluorescence is measured after sufficient time to provide a substantially constant value for said fluorescence.

8. A method according to claim 1, wherein said fluorescence is measured after sufficient time to provide a substantially constant value for said fluorescence.

9. A method for determining the presence of a ligand of from about 125 to 1,000 molecular weight in an unknown which comprises:
   combining in an aqueous assay medium at a pH in the range of 6 to 9 said unknown with antiligand having from about 1 to 20 fluorescein molecules bound to said antiligand;
   contacting said assay medium with an optically transparent surface to which a plurality of ligand analog molecules are bound through poly(amino acid) molecules;
   irradiating said surface on the side opposite said assay medium with light having a wave length within the absorption peak of said fluorescein; and
   determining the amount of fluorescence which is a function of the amount of ligand present in said unknown.

10. An apparatus for carrying out immunoassays, whereby the amount of material present is a function of the amount of fluorescence comprising:
    a light source;
    an immunoassay cell comprising a housing having a chamber, and an optically transparent member having a first surface, to which a plurality of ligands are bound, partially enclosing said chamber, said member being in light receiving relationship and at an angle to said light source to provide total internal reflection, and
    light metering means in light receiving relationship with said member.

11. An apparatus for carrying out immunoassays, whereby the amount of material being assayed is a function of the amount of fluorescence comprising:
    a light source;
    an immunoassay cell comprising a housing having an open top chamber, a transparent slide removably covering said opening, wherein said transparent slide has a first surface to which a plurality of ligands are covalently bound, with said first surface in juxtaposition to said opening;
    a prism over and optically coupled to said slide, wherein said prism and slide are situated in light receiving relationship and at an angle to said light source to provide total internal reflection at said first surface; and
    light metering means in light receiving relationship to said slide for receiving fluorescent light emitted from said slide.

12. An apparatus according to claim 11, wherein said chamber has an optically transparent window extending through said housing.

13. An apparatus according to claim 11, wherein said housing includes recessed supporting means for said slide; and
    means for holding said prism in optical coupling with said slide.

14. A method according to claim 1, wherein said optically transparent surface has a plurality of zones, each zone having a plurality of ligand analogs bound to said surface and wherein the amount of fluorescent light emitted from each of said zones is separately measured.

15. A method according to claim 1, wherein said ligand is a poly(amino acid).

* * * * *